Figure 4:
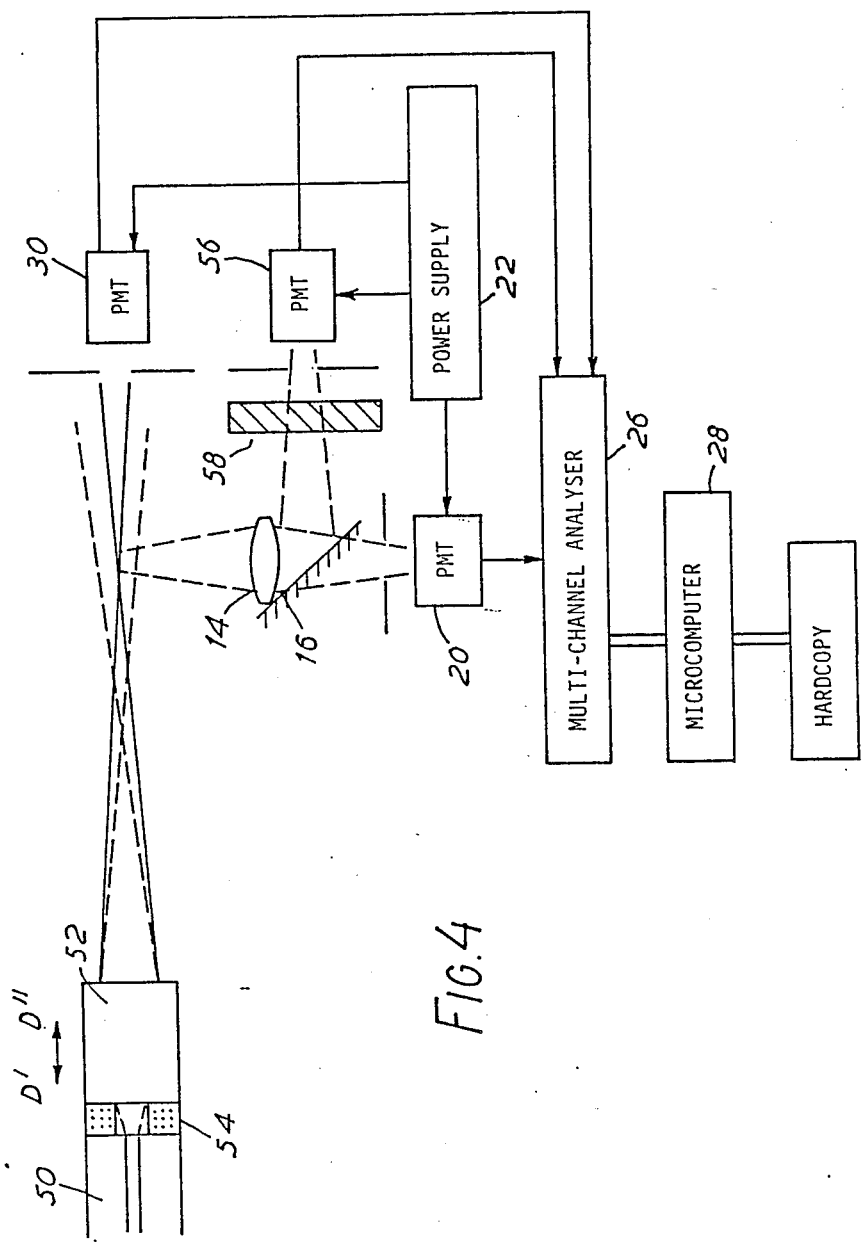

United States Patent [19]

Carr et al.

[11] Patent Number: 4,927,268
[45] Date of Patent: May 22, 1990

[54] OPTICAL ANALYSIS

[75] Inventors: Robert Carr; David J. Clarke; Tony Atkinson, all of Salisbury, United Kingdom

[73] Assignee: Public Health Laboratory Service Board, Salisbury, United Kingdom

[21] Appl. No.: 215,070
[22] PCT Filed: Sep. 7, 1987
[86] PCT No.: PCT/GB87/00627
  § 371 Date: Jul. 5, 1988
  § 102(e) Date: Jul. 5, 1988
[87] PCT Pub. No.: WO88/01736
  PCT Pub. Date: Mar. 10, 1988

[30] Foreign Application Priority Data

Sep. 5, 1986 [GB] United Kingdom ............... 8621426

[51] Int. Cl.$^5$ ............................................. G01N 15/02
[52] U.S. Cl. ................................. 356/336; 356/338; 350/96.18
[58] Field of Search ............... 356/338, 336, 317; 250/227; 350/96.18

[56] References Cited

U.S. PATENT DOCUMENTS

| | | | |
|---|---|---|---|
| 4,387,993 | 6/1983 | Adrian | 356/336 |
| 4,564,598 | 1/1986 | Briggs | 356/317 |
| 4,678,326 | 7/1987 | Harjunman | 356/338 |
| 4,752,131 | 6/1988 | Eisenlauer et al. | 356/338 |
| 4,801,205 | 1/1989 | Tatsuno | 356/343 |
| 4,834,497 | 3/1989 | Angel | 350/96.29 |

FOREIGN PATENT DOCUMENTS 2054143 2/1981 United Kingdom .

OTHER PUBLICATIONS

Applied Optics, vol. 25, No. 5, 1 Mar. 1986 (US), J. C. F. Wang et al.: "In Situ Particle Size Measurements Using A Two-Color Laser Scattering Technique", pp. 653–657, See Paragraph II, . . .
Analytical Chemistry, vol. 58, No. 8, Jul. 1986 (Columbus, Ohio, US).

Primary Examiner—Léon Scott, Jr.
Attorney, Agent, or Firm—Browdy and Neimark

[57] ABSTRACT

Apparatus for optical analysis of particles such as biological cells utilizes twin beams passing through a common optical fibre to avoid problems of alignment. For scattering measurements, a narrower beam can be used to gate detection of a broader beam to avoid amiguities associated with off-axis particles. The twin beams can also be used for thermal lensing, fluorescence or other techniques. Different beam diameters can alternatively be achieved in a single beam by controlling the focal length of a beam focussing lens.

14 Claims, 4 Drawing Sheets

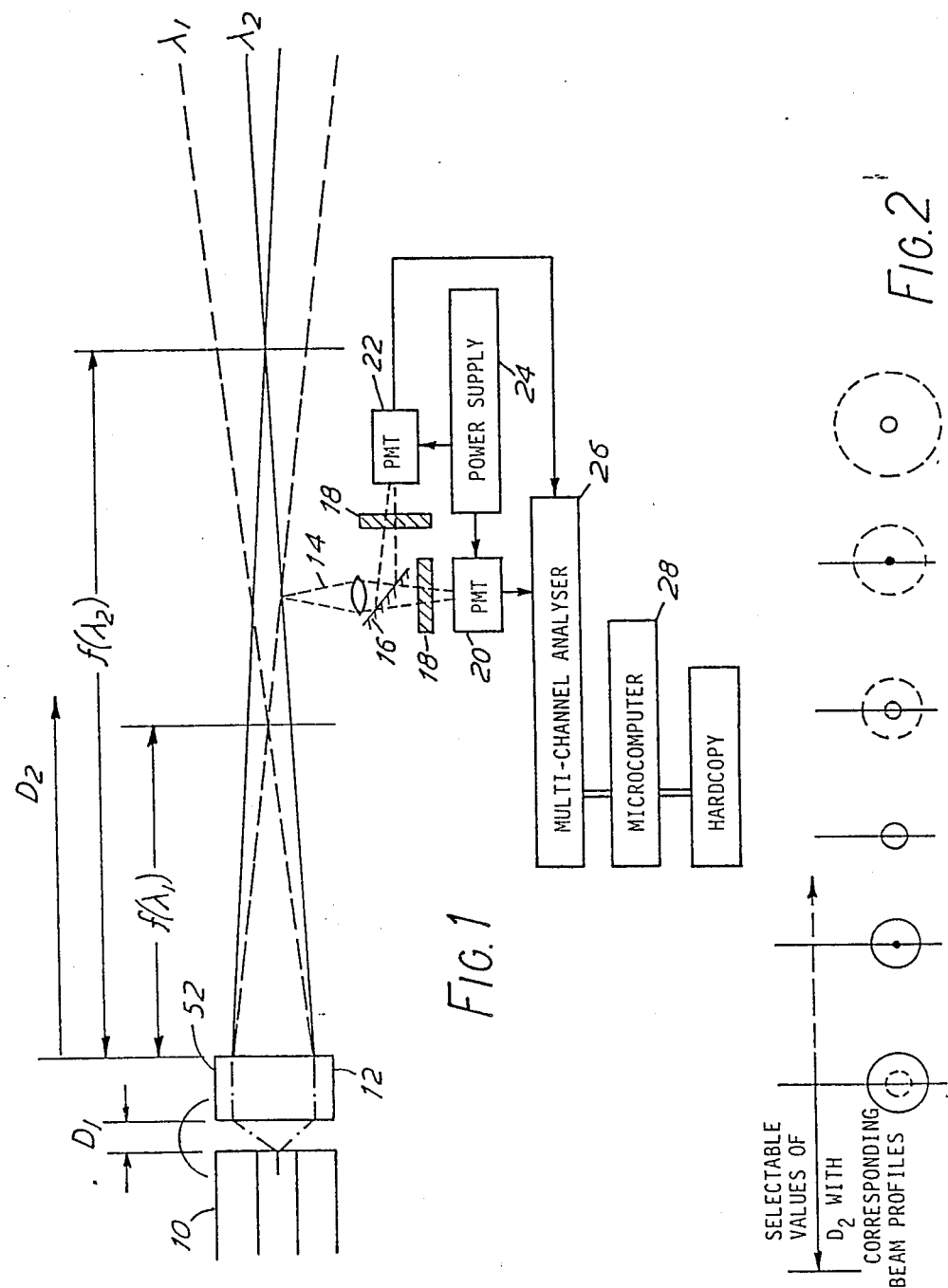

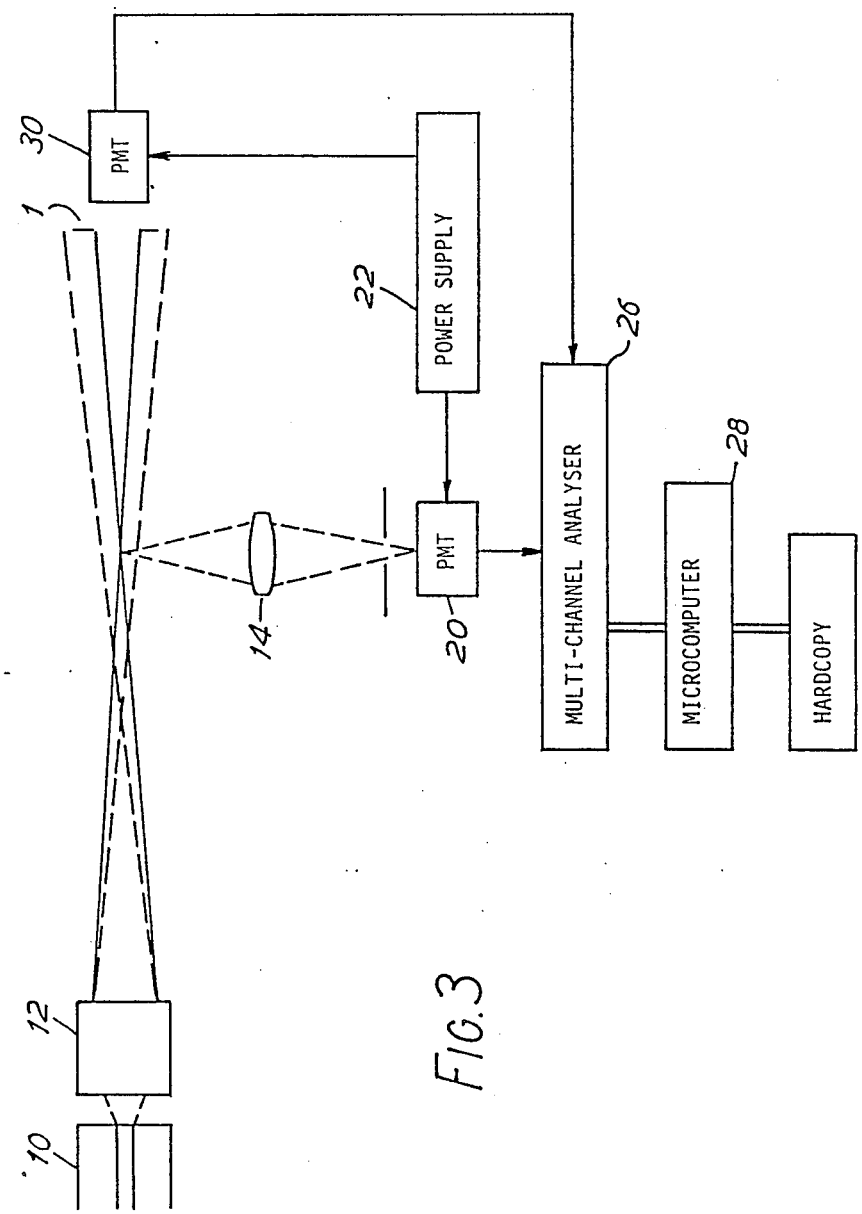

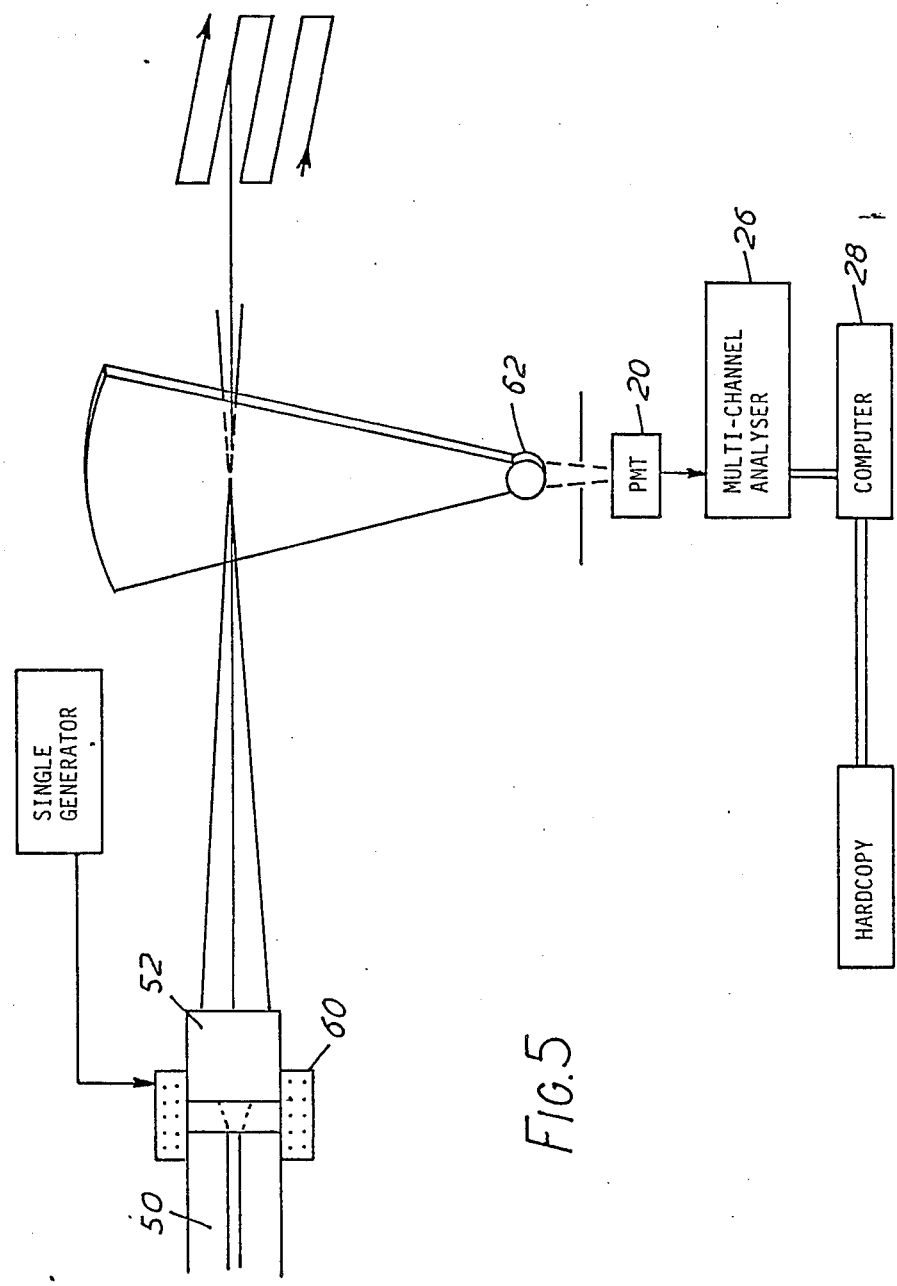

OPTICAL ANALYSIS

This invention relates to optical analysis and in the most important example to the analysis using optical techniques of biological material such as protein or other macromolecules, cells, viruses, tissue fragments and the like.

Over a wide range of particle size—extending from perhaps below a nanometer to around a millimeter—optical methods are favoured for determination of parameters such as particle size, concentration, velocity and shape. The methods that can be used are varied and include scattering, thermal lensing, fluorescence and photophoresis. Known scattering techniques can conveniently be classified as those which utilise:

(i) the diffraction pattern of a population of light scattering particles in the spatial (Fraunhofer) or temporal (photon correlation) mode, or (ii) the intensity of light scattered by an individual particle as it passes through an illuminated scattering volume.

Techniques in the former category tend to require relatively sophisticated optics and computer processing but have proved to be useful with small particles which are all of the same size. Extending the technique to cope with two or more different particle species involves a significant increase in processing capability. The technique is not regarded as practical for use with particle populations which have a large number of different species, such as those occuring in biological systems. It is further the case that Fraunhofer and photon correlation techniques are unsuited for use with larger particles.

The analysis of light scattered by a single particle is inherently more informative as well as being less expensive computationally. The mechanisms by which particles are addressed by the interrogating optical beam can be regarded as falling into two main areas.

In the first technique the fluid sample containing particles of interest is manipulated to form a narrow stream sufficiently small to present only one particle at a time to the scattering volume. It is a disadvantage of this technique that the hydrodynamic sheath required to carry the stream of particles past the measuring zone requires sophisticated fluid handling and the fine orifice from which the particle-containing sample is introduced into the hydrodynamic sheath is notoriously prone to blocking. The equipment is often bulky and requires samples to be separately analysed off-line.

In a second approach, the optical measuring volume is configured to be sufficiently small to address only one particle at a time within a suitably dilute particulate suspension. By using finely focused laser beams, high intensities of light can be concentrated into measuring volumes of less than about $10-3$ microliters.

The analysis of light scattered by a particle passing through a laser beam has the merit of simplicity but the technique suffers from a major draw-back. The light scattered from a relatively large particle which merely "clips" the edge of the beam may be similar to that from a smaller particle passing through the centre of the beam. If these events are not distinguished, the scattering analysis may be ambiguous.

This problem has been overcome in one known arrangement (see for example APPLIED OPTICS Vol. 25 No. 5 pp 653–6571) by using two laser beams of different wavelengths which are configured to be concentrically aligned, one beam being smaller in diameter than the other. The internal beam is disposed centrally of the outer beam. A particle passing through the internal narrow beam is thus known to be, at that instant, central to the outer beam and the resultant scattered light signal from the inner beam is used to trigger or gate the collection of scattered light from the outer beam. In the absence of detected light from the inner beam (this absence being indicative of an off-centre particle) scattered light from the outer beam is ignored. The two signals are differentiated by using two detectors filtered to respond only to one wavelength or the other.

The known system comprises two lasers producing beams which are focused to the required concentric configuration by a combination of lenses, mirrors, beam-splitters and prisms. Each of these optical components requires careful alignment often with three dimensional micrometer adjustment stages. The apparatus is bulky and requires careful handling. It is not regarded as suited to use outside the laboratory and is incapable of on-line analysis of remote samples.

A somewhat similar arrangement is disclosed in GB 2 054 143. This obtains information from the crossing of a localised fringe pattern by the particle of interest. Fringe patterns are set up from two different sets of interfering beams which of different wavelengths and brought to focus at slightly spaced points in space by a dispersing lens system. The fringe patterns are thus of different sizes and the inner pattern can be sued as a trigger or gate as described above. The apparatus is again bulky and poses problems of alignment. It is not well suited to use outside the laboratory.

It is an object of this invention to provide improved apparatus for particle analysis which overcome the mentioned problem of ambiguity but which is suited to use in non-laboratory conditions and is capable of on-line analysis of remote samples.

Accordingly, the present invention consists, in one aspect, in apparatus for optical analysis comprising a detection zone; a common optical fibre for carrying firts and second light beams which are coincident and of distinct wavelengths; a common focusing lens arranged to focus the two beams at respective focal points spaced longitudinally of an axis extending through the detection zone such that in the detection zone the transverse extents of the two beams are in a predetermined ratio and a pair of light detectors focused at the detection zone and capable of distinguishing light scattered from the first and second beams respectively.

Preferably the transverse extent of the second beam is significantly less than that of the first beam; detection of scattered light from the second beam providing an indication that the particle in the detection zone is positioned generally centrally of the first beam.

Advantageously, the common focusing lens is bonded to the free end of the optical fibre means and suitably comprises a gradient index lens.

With the use, according to a preferred form of this invention, of a microlens bonded to the free end of a optical fibre, there is produced a light source which is capable of forming precisely concentric measurement and gating beams, yet which is compact, robust, vibration resistant and well suited to location in remote and possibly hostile situations.

Suitably, means are provided for displacing in unison the beam focal points longitudinally with respect to the detection zone thereby to vary the transverse extent of the respective beams in the detection zone.

According to a further aspect of the invention, there is provided apparatus for particle analysis using light scattered from a single particle in a detection zone, comprising light source means for generating a beam, beam focusing means switchable, at a rate which is fast compared with the transport time of a particle through the detection zone, between measurement and trigger focussing phases in which the beam is focussed at respective focal points spaced longitudinally of said axis such that the transverse extent of the beam in the trigger phase at the detection zone on the beam axis is significantly less than in the measurement phase and scattered light detection means focused at the detection point and synchonised with switching of the beam focussing means, detection of scattered light in the trigger state providing an indication that the particle at the detection point is positioned generally centrally of the beam in the succeeding measurement phase.

In still a further aspect, the present invention consists in a light source for producing concentric light beams having in a transverse plane of interest a selected ratio of beam diameters, comprising an optical fibre; means for launching into the fibre respective beams of different wavelength and a lens mounted at the free end of the optical fibre to bring the respective beams to focus at longitudinally spaced focal points.

Preferably, the lens comprises a gradient index microlens.

Such a light source may have useful applications beyond the analysis of scattered light. One beam might for example comprise a pump beam arranged to cause local heating of a sample having the appropriate absorption spectrum. A change in refractive index on heating can be detected by means of a deflection of the other beam.

The invention will now be described by way of example only with reference to the accompanying drawings in which:

FIG. 1 is a diagrammatic representation of one embodiment of the present invention, FIG. 2 illustrates the effect of an adjustment on the beam diameters in FIG. 1, and FIGS. 3, 4 & 5 are representations, similar to FIG. 1, of further embodiments of the present invention.

Referring to FIG. 1 a light beam of a specific wavelength $\lambda_1$ (for example 488 nm from an air cooled argon ion laser) is launched into an optical fibre 10 in monomode. Light of a second wavelength $\lambda_2$ (for example 632 nm from a helium/neon laser) is either launched into the fibre 10 simultaneously using suitable optical components or is introduced into the fibre at some point intermediate its length by a suitable fibre coupler. In an alternative arrangement, the light can be launched directly into the fibre by "pigtailed" laser diode sources. Since the fibre is only strictly monomode at one wavelength, there may be a departure from a true Gaussian beam profile for the second wavelength.

The two wavelengths of light propagate down the fibre to the free end where they travel for a distance $D_1$ before entering a gradient index microlens 12. The lens 12 may be mounted on the free end of the optical fibre by means of an epoxy resin compound. The mounting may comprise a refractive index matching element. A suitable lens has been found to be "SELFOC" lens SLW 1.8. The dispersive power of the material from which the lens is made will, by chromatic abberation, cause the beams to focus at different distances $F(\lambda_1)$ and $F(\lambda_2)$. The two beams $\lambda_1$ and $\lambda_2$ will as an inherent property of the optical fibre be exactly concentrically aligned. The ratio of the beam diameters will, due to their different focal points, vary with the distance $D_2$ from the microlens. By choosing a particular distance from the microlens, a scattering volume comprising two beams of different beam width can be addressed. The ratio of beam widths can therefore be chosen. Similarly, the beam widths themselves can be selected dependent on $D_2$. As illustrated best in FIG. 2, it is possible by selecting $D_2$ to arrange for either $\lambda_1$ or $\lambda_2$ to be the internal beam. Preferably, the second wavelength is chosen as the internal beam since minor departures from a Gaussian profile can be tolerated, as will be described. The values at the distances $F(\lambda_1)$ and $F(\lambda_2)$ are varied simultaneously by adjusting $D_1$. This also has the effect of changing the beam width ratios for any given value of $D_2$.

The detection system comprises a focussing lens 14, a beam splitter 16, and a pair of filters 18 arranged to present light scattered from the two beams respectively at the measurement detector 20 and gate detector 22. The detectors share a common power supply 24 and provide input signals to a multi-channel analyser 26. A processor 28—which may be commercially available microcomputer—is arranged to look for coincidences in the trigger and measurement channels and conduct appropriate analyses (which may be entirely conventional) upon the signals of the measurement channel.

Since measurements are only made when scattered light is detected from the trigger beam, it is known tha the particle lies generally centrally of the measurement beam. As the internal beam is used only as a trigger, it is not important that the beam profile may not be Gaussian.

In an alternative arrangement, detector optical fibres can be arranged to focus (using microlenses) on each of the beams, and deliver light to remote photodetectors. In a further alternative, a gradient index micorlensed fibre optic identical to that used to form the twin beam is placed at an angle $\theta$ and at a distance equal to D2 from the concentric beams. The scattering volume interrogated by this optical fibre will be coincident with the shape of the beam at this point and is inherent accurately focused for each beam with no adjustment required. This follows from the symetry of the arrangement. Changes in $\theta$ will change the scattering volume.

In arrangements according to the invention, the optical fibre tip incorporating the lens can be positioned in the wall of a sample carrying unit and can if necessary be some distance from the laser sources and signal processing equipment. Particularly if the detector system takes the same form, that portion of the apparatus adjacent to the detection zone can be made extremely compact, robust and vibration resistant and the apparatus is therefore ideally suited to on-line sampling. In a particular application requiring analysis of particles at a number of specific locations, for example in a fermentation process, a number of optical fibre tips acting as sources or detectors can be optically multiplexed from common light sources and signal processing equipment.

As with the known apparatus, the apparatus according to this invention can be used for a variety of different types of analysis. The particle size and size distribution can be determined by analysing the intensity of scattered light and sorting such intensity signals according to particle size to give an accurate indication of particle size distribution. Particle concentration can be determined by counting the number of detected light pulses per unit time. Particle velocity and velocity distribution can be investigated by determining the pulse width as the particle crosses the defined scattering body.

In particular applications, the scattered light can be analysed for spectral characteristics and polarisation. Particles can be specifically labelled with fluorescent molecules or dyes to distinguish the particles of interest. Particle shape can be derived from multi-angle light scattering intensity for given particle size ranges.

The technique of thermal lensing is known and involves, briefly, the selective absorption of a light beam by a sample leading, through localised heating, to changes in refractive index. The refractive index gradient around the site of absorption acts as a lens and can be detected either by monitoring the defocussing of the (partially) absorbed beam or by measuring the deflection of a second beam.

The present invention provides, in a further aspect, apparatus for use in thermal lens analysis. Referring to FIG. 3, components common to the previously described embodiment will not be further described. It will be seen that the detector for the measurement beam is aligned with the beam axis. A thermal lens effect created by absorbtion of the pump beam monitored in detector 30 is measured by determining the degree to which the measurement beam is defocussed.

In a modification to this invention which is illustrated in FIG. 4, light of a signal wavelength is used. The microlens 52 is not fixed in position relative to the end of the optical fibre 50 but can be adjusted using, in the described example, a piezoelectric thickness expander 54. By the application of a square voltage to the thickness expander, the microlens can be displaced between positions D' and D" relative to the fibre. At distance D', the beam is brought into focus at point $F_1$ which may, for example correspond with point $F(\lambda_1)$ of FIG. 2. Similarly, with the lens at position D", the beam is focused at a point $F_2$ corresponding to $F(\lambda_2)$. At a particular distance $D_2$, the thickness of the beam will alternate between a narrow gating beam width and a broad measurement beam width. A single detection system is employed, and this is provided with the same square voltage driving the movement of the microlens.

The signal processing circuit is so arranged that scattered light from the measurement half cycle of the square wave is only processed if scattered light is also detected in the preceding (or succeeding) gating half cycle.

Other gating arrangements could of course be employed. The measurement beam detection will in one example be normally disabled with the microlens normally in the position resulting in a gating beam at the detection zone. Upon detection of scattered light from the gating beam (indicating the arrival of a particle at a central location in the detection zone) the microlens is rapidly shifted to produce a broad measurement beam and the measurement beam detector is enabled. It is of course necessary for the movement of the microlens to occur in a time interval which is short compared with the travel time of the particle across the beam.

Other methods of longitudinally shifting the focal point of the beam can in appropriate cases be employed.

FIG. 4 further illustrates the manner in which this inventions permits several measurements to be made at the same time. This is particularly advantageous with measurements on biological sytems where many varied species of particle may be present. As shown in the figure, detector 30 is arranged to monitor a thermal lens effect whilst detector 56 is provided with a filter 58 to detect fluorescence.

It has been described that in the twin wavelength embodiment of this invention, adjustment of the distance $D_1$ from the optical fibre to the lens can usefully alter the beam widths. Using a mechanism such as the mentioned piezoelectric thickness expander it becomes possible to make such adjustments in real time. Using appropriate processing the caability can be provided of optimising the width of the measurements beam in real time in dependence upon the size of the particle detected.

It is also possible to use a piezoelectric element to effect xy scanning of the beams. As shown in FIG. 5, a piezoelectric effect element 60 is arranged by means of a suitable signal generator to produce a raster scan through the area of interest. To simplify the detecting optices, a cylindrical lens is used to provide a fan shaped detection zone.

It should be understood that this invention has been described by way of example a wide variety of modifications are possible without departing from the scope of the appended claims. The described methods of producing twin beams will, for example find application in other analytical techniques or combinations of techniques beyond those specifically described. The examples should be quoted of sphotphoresis, where movement of a particle on absorbtion or scattering of light is detected optically, and optical trapping of particles.

Reference has been made in this description to "particles". This term is intended to be interpreted broadly to cover liquid droplets and also optical discontinuities in a field of view.

We claim:

1. Apparatus for optical analysis comprising a detection zone; a common optical fibre for carrying first and second laser beams which are mutually coincident and of different wavelengths; a common focusing lens arranged to focus the two beams at respective focal points spaced longitudinally of an axis extending through the detection zone, such that in the detection zone the transverse extents of the two beams are different and in a predetermined ratio, and a pair of light detectors focused at the detection zone and responsive respectively to light scattered from the first and second laser beams.

2. Apparatus according to claim 1, wherin the common focusing lens is bonded to an end of the optical fibre proximal the detection zone.

3. Apparatus according to claim 2, wherein means are provided for displacing in unison said focal points longitudinally with respect to the detection zone thereby to vary the transverse extent of the respective beams in the detection zone.

4. Apparatus according to claim 1, wherein the common focussing lens comprises a gradient index lens.

5. Apparatus according to claim 4, wherein means are provided for displacing in unison said focal points longitudinally with respect to the detection zone thereby to vary the transverse extent of the respective beams in the detection zone.

6. Apparatus according to claim 1, wherein means are provided for displacing in unison said focal points longitudinally with respect to the detection zone thereby to vary the transverse extent of the respective beams in the detection zone.

7. Apparatus for particle analysis using light scattered from a single particle moving through a detection zone, comprising light source means for generating a beam, beam focussing means switchable, at a rate which is fast compared with the time taken for the particle to move through the detection zone, between measurement and trigger phases in which the beam is focussed at respective focal points spaced longitudinally of said axis such that the transverse extent of the beam in the trigger phase at the detection zone on the beam axis is significantly less than in the measurement phase and scattered light detection means focussed at the detection zone and synchronised with switching of the beam focussing means, detection of scattered light in the trigger phase providing an indication that the particle at the detection zone is positioned generally centrally of the beam in said measurement phase.

8. Apparatus according to claim 7, wherein detection of scattered light in the trigger phase serves to trigger switching of the focussing means to the measurement phase.

9. Apparatus according to claim 8 wherein the light source means comprises laser means and an optical fibre and wherein the beam focussing means comprise a lens movable in position relatively to an end of the optical fibre proximal the detection zone.

10. Apparatus according to claim 7 wherein the light source means comprises laser means and an optical fibre and wherein the beam focussing means comprise a lens movable in position relatively to an end of the optical fibre proximal the detection zone.

11. Apparatus according to claim 10, wherein said lens is mounted on said end of the optical fibre by means of a piezoelectric element.

12. A light source for producing concentric light beams having in a transverse plane of interest a selected ratio of beam diameters, comprising an optical fibre; means for launching into the fibre respective beams of different wavelength and a lens mounted at the free end of the optical fibre to bring the respective beams to focus at longitudinally spaced focal points.

13. Apparatus according to claim 10, wherein the lens comprises a gradient index microlens.

14. Apparatus for particle analysis utilising light scattered from a single particle in a detection zone, comprising optical fibre means for carrying measurement and gating light beams which are coincident and of distinct wavelengths; a common focusing lens arranged to focus the two beams at respective focal points spaced longitudinally of an axis extending through the detection zone such that in the detection zone the transverse extent of the gating beam is significantly less than that of the measurement beam; and scattered light detection means focused at the detection zone and capable of distinguishing light scattered from the measurement and gating beams respectively, detection of scattered light from the gating beam providing an indication that the particle in the detection zone is positioned generally centrally of the measurement beam.

* * * * *